United States Patent [19]

Kim et al.

[11] Patent Number: 5,750,340
[45] Date of Patent: May 12, 1998

[54] IN SITU HYBRIDIZATION SOLUTION AND PROCESS

[75] Inventors: In C. Kim; Donald M. Thompson; Gloria E. Sarto, all of Albuquerque, N. Mex.

[73] Assignee: University of New Mexico, Alburquerque, N. Mex.

[21] Appl. No.: 418,704

[22] Filed: Apr. 7, 1995

(Under 37 CFR 1.47)

[51] Int. Cl.$^6$ .............................. C12Q 1/68; A61K 9/44; G01N 1/30
[52] U.S. Cl. ........................... 435/6; 435/40.5; 435/40.52
[58] Field of Search ............................. 435/6, 40.5, 40.52

[56] References Cited

U.S. PATENT DOCUMENTS

| | | | |
|---|---|---|---|
| 4,302,204 | 11/1981 | Wahl et al. | 23/230.3 |
| 4,358,535 | 11/1982 | Falkow et al. | 435/5 |
| 4,647,529 | 3/1987 | Rodland et al. | 435/6 |
| 4,689,294 | 8/1987 | Boguslawski et al. | 435/6 |
| 4,886,741 | 12/1989 | Schwartz | 435/5 |
| 4,888,278 | 12/1989 | Singer et al. | 435/6 |
| 5,132,207 | 7/1992 | Kohne et al. | 435/6 |
| 5,225,326 | 7/1993 | Bresser et al. | 435/6 |
| 5,232,831 | 8/1993 | Milliman et al. | 435/6 |
| 5,316,906 | 5/1994 | Haugland et al. | 435/4 |
| 5,447,841 | 9/1995 | Gray et al. | 435/6 |
| 5,506,098 | 4/1996 | Zarling et al. | 435/6 |
| 5,512,436 | 4/1996 | Stone | 435/6 |
| 5,521,061 | 5/1996 | Bresser et al. | 435/517 |
| B1 4,358,535 | 5/1986 | Falkow et al. | 435/5 |

FOREIGN PATENT DOCUMENTS

| | | |
|---|---|---|
| WO 90/02204 | 8/1990 | WIPO . |
| WO 95/03431 | 2/1995 | WIPO . |

OTHER PUBLICATIONS

Visakorpi et al. (1994) Am. J. Pathol. 145:624–630.
Chang (1994) J. Immunol. Methods 176:235–243.
Florijn et al. (1995) Cytometry 19:177–182.
Hyytinen et al. (1994) Cytometry 16:93–99.
Griffin, D.: "Fluorescent in Situ Hybridization for the Diagnosis of Genetic Disease at Postnatal, Prenatal, and Preimplementation Stages"—*International Review of Cytology* vol. 153(1994) Academic Press, Inc.
Haar, F.M. et al.: "A Rapid FISH Technique for Quantitative Microscopy" *Biotechniques Research Reports vol. 17, No. 2* (1994) pp. 346–353.
Klinger, K. et al.: "Rapid Detection of Chromosome Aneuploidies in Uncultured Amniocytes by Using Fluorescence in Situ Hybridization (FISH)"—*Am. Human Genet. 51:55–65*, (1992).
Kuo, W.L., et al. : "Detection of Aneuploidy Involving Chromosomes 13, 18, or 21, by Fluorescence In Situ Hybridization (FISH) to Interphase and Metaphase Amniocytes"—*Am. J. Hum. Genet.* 49:112–119, (1991).
Ward, B., et al.: "Rapid Prenatal Diagnosis of Chromosomal Aneuploidies by Fluorescence In Situ Hybridization: Clincal Experience with 4,5000 Specimens"—*Am. J. Hum. Gent* 52:854–865, 1993.
Yang, T.T., et al.—"Fast Hybridization Solution for the Detection of Immobilized Nucleic Acids" vol. 18 No. 3 (1995) Biotechniques Research Reports pp. 498–503.
Clontech Laboratories, Inc.: "Express Hybridization Solution" (PT1190–1) Catalog # 8015—1—Product Protocol Cover sheet and pp. 5, 7, 9, 11.
PAMPHLET: CyProbe (Chromosome Detection Sequences) Cat. No. A6300X (Biological Detction Systems, Inc.).
Material Safety Data Sheet—'Formamide' pp. 1–4—Fisher Scientific, Inc. (1995).
BROCHURE: Oncor Detection Kit: Rapid Chromosome in Situ Hybridization System (Rapid Hybridization Protocol for Direct–Labeled (FITC or Texas Red) Satellite DNA Probes) (1993) Oncor, Inc. pp. 1–13.
PAMPHLET: Imagentics Spectrum CEP Direct Chromosome Enumeration System (Procedural Kit) Imagentics, Inc.

*Primary Examiner*—W. Gary Jones
*Assistant Examiner*—Amy Atzel
*Attorney, Agent, or Firm*—Deborah A. Peacock; Jeffrey D. Myers; G. Dickson Kehl

[57] ABSTRACT

A fluorescence in situ hybridization (FISH) procedure and solutions is provided. The entire FISH procedure is fast (15 minutes or less), with the hybridization step occurring in 5 minutes or less. The entire FISH procedure with digoxygenin- or biotin-labeled probes takes approximately 30 minutes. A formamide-free solution (dextran sulfate and glycerol) is provided. An additional solution (10% dextran sulfate and 20% formamide) is also provided. Additional solutions are provided for mRNA in situ hybridization whereby the process takes less than 24 hours.

23 Claims, No Drawings

IN SITU HYBRIDIZATION SOLUTION AND PROCESS

BACKGROUND OF THE INVENTION

1. Field of the Invention

This invention relates to fluorescence in situ hybridization.

2. Background Art

In situ hybridization (ISH) is a powerful and versatile tool for the detection and localization of nucleic acids (DNA and RNA) within cell or tissue preparations. By the use of labeled DNA or anti-sense RNA probes, the technique provides a high degree of spatial information in locating specific DNA or RNA sequences within individual cells or chromosomes. ISH is widely used for research and potentially for diagnosis in the areas of prenatal genetic disorders, and molecular cytogenetics. In the general area of molecular biology, ISH is used to detect gene expression and over-expression, to map genes, to identify sites of gene expression, to localize target genes, and to identify and to localize various viral and microbial infections. Currently, the application of the ISH technology research is being expanded into tumor diagnosis, preimplantation genetic diagnosis for in vitro fertilization, evaluation of bone marrow transplantation, and analysis of chromosome aneuploidy in interphase and metaphase nuclei.

In ISH, labeled nucleic acids (DNA or anti-sense RNA) are hybridized to chromosomes or mRNAs in cells which are immobilized on microscope glass slides (*In Situ Hybridization: Medical Applications* (eds. G. R. Coulton and J. de Belleroche), Kluwer Academic Publishers, Boston (1992); *In Situ Hybridization: In Neurobiology; Advances in Methodology* (eds. J. H. Eberwine, K. L. Valentino, and J. D. Barchas), Oxford University Press Inc., England (1994); *In Situ Hybridization: A Practical Approach* (ed. D. G. Wilkinson), Oxford University Press Inc., England (1992)). Numerous non-isotopic systems have been developed to visualize labeled DNA probes including; a) fluorescence-based direct detection methods, b) the use of digoxigenin- and biotin-labeled DNA probes coupled with fluorescence detection methods, and c) the use of digoxigenin- and biotin-labeled DNA probes coupled with antibody-enzyme detection methods. When fluorescence-labeled nucleic acid (DNA or RNA) probes are hybridized to cellular DNA or RNA, the hybridized probes can be viewed directly using a fluorescence microscope. By using multiple nucleic acid probes with different fluorescence colors, simultaneous multicolored analysis (i.e., for multiple genes or RNAs) can be performed in a single step on a single target cell. Fluorochrome-directly labeled nucleic acid probes eliminate the need for multi-layer detection procedures (e.g., antibody-based system), which allows fast processing and also reduces non-specific background signals. Therefore, fluorescence in situ hybridization (FISH) has become an increasingly popular and valuable tool in both basic and clinical sciences.

Because of the importance of FISH technology in molecular biology and cytogenetics, optimizing current FISH technology to improve the sensitivity of hybridization (fluorescence) signals, to simplify and thus decrease the time for the process, and to substitute toxic reagents with non-health hazard chemicals used in the FISH process is desirable. FISH technology for DNA (or RNA) chromosomes is dependent on four major factors: (a) optimal temperature for effective denaturation of double strand DNAs (separation of two DNA strands), (b) optimal temperature for annealing or hybridization between target DNA (or RNA) and labeled DNA or RNA probes (i.e., DNA or anti-sense RNA fragments with which enzymes, fluorochromes, chromophores, chemiluminescers, bioluminescers, radioisotopes, biotin or avidin are conjugated), (c) selection of suitable solutions to enhance both the denaturation and the hybridization processes, and (d) effective post-hybridization washing conditions. It is essential that the structural integrity of nuclei, chromosomes, cells, tissue sections and spatial resolution of the fluorescence signals not be compromised during the FISH process. Therefore, optimization of FISH technology should include increased hybridization efficiency, increased detection sensitivity, and preservation of cellular, tissue, nuclear, and chromosomal morphology.

Currently, FISH procedures performed by many laboratories around the world are generally very similar to those of Kuo, et al., ("Detection of Aneuploidy Involving Chromosomes 13, 18 or 21, by Fluorescence in Situ Hybridization to Interphase and Metaphase Amniocytes," *Am. J. Hum. Genet.* 49: 112–119 (1991); Klinger, et al., "Rapid Detection of Chromosome Aneuploidies in Uncultured Amniocytes by Using Fluorescence in Situ Hybridization (FISH)," *Am J. Hum. Genet.* 51: 55–65 (1992); and Ward, B. E., et al., "Rapid Prenatal Diagnosis of Chromosomal Aneuploidies by Fluorescence in Situ Hybridization; Clinical Experience with 4,500 Specimens," *Am. J. Hum. Genet.* 52: 854–865 (1993)). However, most laboratories rely, for convenience on kits available from two major commercial sources: Oncor, Inc., "Rapid Chromosome In Situ Hybridization System: Edition 1, October, 1993; and Imagenetics/Vysis, Inc., 31 New York Ave., Framingham, Mass. 01701. Biological Detection Systems provides only labeled DNA probes with a recommended FISH protocol: Biological Detection Systems, Inc., 955 William Pitt Way, Pittsburgh, Pa. 15238. All of these FISH procedures are time consuming, labor intensive, extremely tedious, and of very limited detection sensitivity. U.S. Pat. No. 5,225,326, to Bresser, et al. teaches "one step in situ hybridization," wherein both fixation and FISH can purportedly be performed in 5 minutes to 4 hours. Haar, et al., "A Rapid FISH Technique for Quantitative Microscopy," *Bio Techniques*, Vol. 17, No. 2, pp. 346–353 (August 1994), discloses a technique which can "in principle" reduce the time necessary for FISH to thirty minutes.

Scoring fluorescence signals using the FISH procedures described above, generally requires a 100× oil-immersion objective lens with a triple bandpass filter due to lower signal sensitivity. The use of a high concentration of formamide during FISH process appears to incur morphological destruction of cellular, nuclear or chromosomal structure. Furthermore, all of these processes involve the use of formamide during hybridization or post-hybridization process. Formamide is an expensive, toxic solvent and also a teratogen. Therefore, a formamide-free FISH process is environmentally and hygienically desirable.

SUMMARY OF THE INVENTION

A rapid, simple, and highly sensitive fluorescence in situ hybridization (FISH) procedure was developed on the basis of two preferred denaturation-hybridization solutions: 1) with formamide: 10% dextran sulfate/20% formamide/0.9% NaCl or KCl solution, and 2) formamide-free: 10% dextran sulfate/20% glycerol/0.9% NaCl or KCl solution. For RNA-FISH, solutions 1 and 2 may be modified by dissolving the dextran sulfate in 0.1% diethylpyrocarbonate (DEPC) water to produce solutions F-DEPC (solution 1 plus DEPC) and G-DEPC (solution 2 plus DEPC). Labeled nucleic acid (DNA or anti-sense RNA) probes were dissolved in one of these two denaturation-hybridization solutions. The solution containing the labeled probes was applied to nuclei or appropriately treated cells and tissue sections which were immobilized on microscopic glass slides and then glass coverslips were gently placed to allow uniform spreading of the probe solution.

Labeled nucleic acid probes and nucleic acids in chromosomes and appropriately treated cells and tissue sections on the glass slides were simultaneously denatured for approximately 1.5±0.5 minutes in an oven of approximately 100° C.±5° C. with or without a sealant between coverslip and glass slide, and then immediately hybridized in an oven at a temperature of approximately 55° C.±5° C. for 5 minutes.

After removing the coverslips from the slides, the hybridized slides were washed in 50% formamide in 0.45% NaCl for 3 minutes at 38° C., and then for 5 minutes in 0.9% NaCl at 38° C. Alternatively, the hybridized slides were washed in formamide-free 0.1–0.2% NaCl at 60° C. for 5 minutes and then for another 3 minutes in new 0.1–0.2% NaCl at 60° C.

After air-drying, slides were counterstained with 4,6-diamidino-2-phenylindole (DAPI) or propidium iodide (PI) solution. Fluorescence signals were visualized with a fluorescence microscope which was equipped with a triple band-pass filter and a 20× or 40× dry objective lens. The whole FISH process took from 5 minutes to 15 minutes. Advantages of these procedures which are based on these two denaturation-hybridization solutions are: 1) elimination of the step of sealing coverslip to slide with rubber cement during the entire FISH process; 2) simplification of FISH processing steps by co-denaturation (an ability to vary the temperatures +/−10 degrees without negatively affecting the outcome); 3) a rapid FISH process in 15 minutes or less; 4) highly increased sensitivity of hybridization (fluorescence) signals; and 5) development of an entirely formamide-free fluorescence in situ hybridization process. In addition, this process can be used for other non-fluorescence in situ hybridization processes.

It is a primary object of the present invention to provide several solutions which result in highly sensitive, fast (hybridization within 15 minutes, and all steps of prehybridization, hybridization and post-hybridization within 24 hours), technically easy, reliable FISH procedures. It is another object of the invention to provide a formamide-free FISH solution and procedure.

Advantages of the invention are the use of simple, efficient and environmentally safe solutions for FISH procedures.

Other objects, advantages and novel features, and further scope of applicability of the present invention will be set forth in part in the detailed description to follow, and in part will become apparent to those skilled in the art upon examination of the following, or may be learned by practice of the invention.

DESCRIPTION OF THE PREFERRED EMBODIMENTS

(BEST MODES FOR CARRYING OUT THE INVENTION)

The present invention includes several areas of improvements of current FISH technology: (a) development of simple denaturation-hybridization solutions which facilitate the FISH process in approximately 15 minutes with very high sensitivity and high retention of morphology; and (b) development of an entirely formamide-free FISH technique. The present invention permits the detection of one copy of target genes or RNA in cultured cells, tissue sections, tumors, and on nitrocellulose or nylon paper for use in association with blotting technology. The present invention permits the detection of signals in interphase nuclei, using more dilute solutions of the probe than suggested in prior art (Oncor, Inc.; Imagenetics/Vysis Inc.; BDS, Inc.), thus decreasing the cost of the procedure and increasing the likelihood that screening large populations would be cost effective. The present invention allows the entire procedure to be accomplished at varying temperatures and times, without negatively affecting the signal detection, and makes the whole process more forgiving of minor deviations and thus applicable to processing large numbers of samples. The quickness (15 minutes) and reliability with which FISH can be accomplished with the present invention makes it applicable to those instances where speed is of the essence, e.g., preimplantation genetics.

Currently, the most widely used commercial kits include or suggest hybridization buffers containing formamide and SSC (saline sodium citrate) with or without dextran sulfate. When various commercial kits were used for FISH according to the provided protocols, hybridization signals were barely detectable with a 40× objective lens. Thus, enumeration of signals in prior art normally requires a 100× oil immersion objective lens. Therefore, it appears that use of formamide and SSC with and without dextran sulfate according to the provided protocols is less effective in hybridization and requires longer hybridization time (preferably overnight). Therefore, the present invention provides a highly effective medium for hybridization.

Prior art FISH technologies, available from commercial sources, take at least two hours to more than 12 hours. In addition, those procedures involve various laborious steps, separate denaturation of target nucleic acids and labeled probes, separate denaturation and hybridization procedures, and repeated dehydration of target nucleic acids with graded alcohols, etc.

The present invention, in contrast, involves only three steps and results in a high detection sensitivity: denaturation (approximately 1.5±0.5 minutes), hybridization (approximately 5 minutes or less), and post-hybridization wash (approximately 8 minutes). Therefore, it takes only a total of approximately 15 minutes to perform the FISH process of the present invention (see Example 1). Conventional FISH procedures require precise timing and temperature for the denaturing and hybridization processes. The present invention allows variation in the time and temperature with little effect on the high degree of sensitivity.

Conventional FISH procedures require the use of an oil-immersion 100× objective lens for adequate enumeration of signals. Because of the optimal composition of the denaturation-hybridization solutions and optimal denaturation-hybridization conditions (temperature and timings), the fluorescence signals become very bright. Therefore, enumeration of signals can be performed with a 20× or 40× dry objective lens with a triple bandpass filter after the 15 minute-FISH with the present invention.

Commonly, SSC (saline sodium citrate) is used during the FISH process. With SSC, the pH must be adjusted to around 7.0. Preparation of SSC is a time consuming process. Although, SSC may be used instead of the saline with the present invention, in the present invention, SSC may be entirely replaced with saline. There is no need for adjusting the pH of saline for post-hybridization washings, thus shortening and simplifying the FISH process.

The preferred solution of the present invention, known as solution G, comprises a formamide-free mixture of 10%±2% by weight dextran sulfate and 15%–25% (preferably 20%) glycerol and 0.9% by weight NaCl, KCl or other salt. A 10%–20% dextran sulfate solution or 20–50% glycerol solution alone, mixed with labeled nucleic acid probes, will not result in effective hybridization. However, the present invention's combination of glycerol and dextran sulfate enhances the hybridization remarkably. The efficiency of the hybridization depends mainly on the concentration of glycerol. As glycerol concentration increases above 30%, hybridization signals decrease, probably due to the increased viscosity of the solution. However, inclusion of glycerol in the probe solution prevents drying throughout the hybridization process (e.g. up to 15 hours at 38° C.) without the need for sealing with rubber cement. As viscosity increases, hybridization signals become weaker resulting in the need for increased denaturation-hybridization times and temperatures to obtain optimal fluorescence signals. Glycerol and dextran sulfate are relatively inert chemicals. Therefore, solution G is a more desirable solution.

An alternative solution of the invention, known as solution F, comprises 10%±2% by weight dextran sulfate, 10–30% (preferably 20%) by volume formamide and 0.9% by weight NaCl, KCl or other salt. The formamide is only effective for hybridization in conjunction with the dextran sulfate. Formamide concentrations lower than 15% or higher than 25% can be used for fluorescence in situ hybridization, but the use of these formamide concentrations requires different denaturation temperature settings, different denaturation times, different hybridization temperature settings, and different hybridization times. For example, these conditions require 38° C. in a humidified incubator for a much longer time (preferably overnight) to complete the FISH process. Furthermore, the longer incubation time requires sealing the coverslips and glass slides with tight rubber cement in order to avoid uptake of moisture or evaporation of FISH solution. Therefore, the preferred formamide concentration is 20%±5% by volume. In addition, a higher concentration of formamide (above 35%) promoted structural destruction of cellular and nuclear morphology.

The present invention does not require sealing coverslips with rubber cement during any step of the FISH assay although rubber cement or other sealants may be utilized. In prior art, hybridization signals become weak if the seal with rubber cement is broken. Therefore, applying rubber cement must be done carefully, is tedious, and requires 30–60 minutes before denaturation. The rubber cement seals must be removed before initiation of post-hybridization washings. Therefore, sealing with rubber cement and removing seals are inconvenient nuisances and, with a large number of samples, can be extremely time consuming. The present invention eliminates these laborious and tedious procedures (e.g., sealing and removing of rubber cement) without interfering with the hybridization process. Therefore, the present invention is very easy and convenient to perform.

After the denaturation-hybridization process, hybridized slides are preferably washed with formamide-free 0.1 to 0.2% NaCl solution. Non-specifically bound or excess unbound probes are effectively removed under these conditions. Therefore, by using solution G, entirely formamide-free FISH can be accomplished. Since formamide is toxic and expensive, a formamide-free FISH assay is environmentally and economically desirable.

The above description of the present invention defines the optimal conditions for DNA under which the whole FISH process can be completed in 15 minutes and allows enumeration of signals in interphase nuclei with a 20× or 40× dry objective under a triple bandpass filter. Other conditions may be used, for example, any temperature for denaturation and hybridization can be used, as long as the temperature does not exceed approximately 110° C. Under these "other conditions" enumeration of signals require a 60× dry objective lens in conjunction with 10× eyepieces, but still does not require a 100× oil immersion lens. These other conditions for FISH are defined below:

(a) With solution G: Glycerol concentration from 35–50% with 10% dextran sulfate, denaturation conditions can range from 75° C. to 90° C. for 5 minutes to 1 minute respectively. Hybridization conditions range from 45° C. to 38° C. for 30 minutes to overnight (with or without rubber cement).

(b) With solution F: Denaturation temperature can range from 75° C. to 90° C. for over 2 minutes to 1 minute respectively. Hybridization conditions range from 45° C. to 38° C. for 30 minutes to overnight. The overnight incubation requires sealing of the coverslips with rubber cement.

(c) With solution F-DEPC: The solutions contained approximately 8 and 12% by weight dextran sulfate dissolved in 0.1% Diethylpyrocarbonate (DEPC) water, between approximately 10 and 30% by volume formamide and a salt. There was no need to denature RNA. The hybridization time was from 1 hour to 24 hours at 75° C. Sealing the cover glass with rubber cement was needed for hybridization times greater than 2 hours.

(d) With solution G-DEPC: The solution contained between approximately 8 and 12% by weight dextran sulfate dissolved in 0.1% DEPC water, between approximately 15 and 25% by weight glycerol and a salt. There was no need to denature RNA. The hybridization time was from 1 hour to 24 hours at 75° C. Sealing the cover glass with rubber cement was needed for hybridization times greater than 2 hours.

INDUSTRIAL APPLICABILITY

The invention is further illustrated by the following non-limiting examples.

EXAMPLE 1

FISH performed with F and G solutions on various cell and tissue samples with simultaneous denaturation of sample and probes, hybridization and formamide and formamide free washings.

1) Materials

A mixed probe of Rhodamine-labeled specific DNA for X chromosome and FITC (fluorescein isothiocyanate)-labeled specific DNA for Y chromosome probes (or Rhodamine-labeled Y chromosome and FITC-labeled X-chromosome DNA probes) were obtained from a commercial source (Oncor, Inc., Imagenetics/Vysis, Inc., BDS, Inc.). The probes were diluted with various denaturation-hybridization solutions (see below).

2) Preparation of Cell and Tissue Samples a) Leukocytes were obtained from peripheral blood as follows: Freshly collected blood from donors was subjected to routine Histopaque centrifugation. Mononuclear and granulocyte cells were combined and washed once with PBS (phosphate buffered saline). The washed cell pellets were treated with cold methanol/ acetic acid (3:1), and kept at −20° C. until use for FISH.

b) Metaphase spreads or interphase cells of cultured and uncultured peripheral lymphocytes were immobilized on the glass slides according to standard cytogenetic procedures; methanol/acetic acid treated cells were placed on glass slides. Slides were air dried.

c) 5% paraformaldehyde-treated cells were treated with cold methanol/acetic acid (3:1), and kept at −20° C. for at least 30 minutes. Then, the methanol/acetic acid treated cells were applied on glass slides. When the slides were dried, proteinase K (50 µg/ml) was applied to the cell smear and incubated for 10 minutes at 38° C. Then the slides were washed with 0.05M Tris buffer, pH 7.4, and then air dried.

d) Paraformaldehyde-fixed, paraffin-embedded tissue sections were deparaffinized according to the standard procedures (with xylene and graded alcohols). The deparaffinized sections were treated with proteinase K as described above The slides were air dried.

3) Preparation of Denaturation-hybridization Solutions: solutions F and G a) Solution F: Formamide-containing denaturation hybridization solution.

Solution F contained 10%±2% by weight dextran sulfate, 20%±10% (preferably 20%) by volume formamide, and 0.9% saline (e.g. NaCl or KCl) as follows: (Preferred) 1 gram of dextran sulfate and 0.09 grams of NaCl or KCl were dissolved in 8 ml of deionized water and then 2 ml of formamide were added. The solution was thoroughly mixed, and stored at −20° C. until use.

b) Solution G: Formamide-free denaturation-hybridization solution

Solution G contained 10%±2% by weight dextran sulfate, 20%±5% (preferably 20%) by weight glycerol, and 0.9% by weight saline (e.g. NaCl or KCl) as follows: (Preferred) 1 gram of dextran sulfate and 0.09 gram of NaCl or KCl were dissolved in 8 ml of deionized water and then 2 ml of glycerol were added. The solution was thoroughly mixed, and stored at −20° C. until use.

4) Simultaneous Denaturation of Samples and Probes

In this invention, "labeled probes" represent DNA or anti-sense RNA to which relatively heat-stable enzymes and ligands, fluorochromes, (e.g., FITC, rhodamine, Texas Red) chromophores, chemiluminescers, bioluminescers, or radioisotopes were covalently conjugated. The labeled probes were diluted with solution F or G to an appropriate concentration. Thus, the "probe solution" represents labeled probes (Oncor, Inc.; Imagenetics/Vysis, Inc., BDS, Inc.) which were diluted in solutions F or G. (See Example 2, Table I).

5 to 30 µl of the diluted probe solution were spotted on nuclei, or appropriately treated cells or tissue sections on the glass slides. A glass coverslip was gently applied to cover the probe solution and slight pressure applied to assure uniform spread of the probe solution over the sample area. Sealing between the coverslip and glass slide with rubber cement was not necessary. The slides were put into an oven of 95° C.–105° C. (100° C.±5° C.) and denatured for 1.5±0.5 minute. During this period, both target nucleic acids and labeled probes appeared to be simultaneously and effectively denatured in the presence of the unique F or G solution.

5) Hybridization

Following denaturation, the slides were transferred into another oven of 55° C.±5° C., and hybridized for approximately 5 minutes. Alternatively, if only one oven was available, the hot aluminum shelf with the slides on it, was removed from the oven and placed in a drawer of the laboratory bench and kept at ambient temperature for approximately 5 minutes to cool the temperature spontaneously. In either case, during this 5 minute period, single stranded target DNA and probes were hybridized with a maximum efficiency in the presence of the unique F or G solution. Hybridization for up to 20–30 minutes increased the hybridization signals slightly more, but it was determined that the 5 minute incubation was adequate for microscopic detection of hybridization signals with a 20× or 40× objective lens. (See Example 2, Table II).

6) Post-hybridization Washings

After hybridization, the coverslips were removed from glass slides. The slides were then subjected to one of the following post-hybridization washings to remove non-specifically bound probes:

a) Formamide-containing washings: The hybridized slides were immersed in 50% formamide solution containing 0.45% NaCl for 3 minutes at 38° C., and subsequently in 0.9% NaCl for 5 minutes.

b) Formamide-free washings: The hybridized slides were immersed in 0.1%–0.2% NaCl for 5 minutes and then for another 3 minutes in new 0.1%–0.2% NaCl solution.

7) Visualization of Fluorescence in Situ Hybridization Signals

After post-hybridization washings, slides were air dried. Then, a small amount of counterstain (200 ng/ml of propidium iodide (PI) or 20 ng/ml of 4,6-diamidino-2-phenylindole (DAPI) in antifade) was spotted on the slide to counterstain nuclei. Hybridization signals in the nuclei were viewed using an Olympus inverted fluorescence microscope (Model IMT-2) which was equipped with a triple bandpass filter and a 100 watt mercury lamp and 10X, 20X, 40× and 60× dry objective lenses, in conjunction with 10× eyepieces. Under experimental conditions, no oil immersion lens was necessary. Signal enumeration by fluorescence was adequately performed with a 20× or 40× dry objective lens.

EXAMPLE 2

Identification of denaturation/hybridization solutions, denaturation/hybridization time and temperatures, resulting in enumeration of fluorescence signals in interphase nuclei with 20× and 40x dry objective lenses.

In this example, a mixed probe was used containing rhodamine-conjugated × and FITC-conjugated Y chromosome probes (or rhodamine-conjugated Y and FITC-conjugated × chromosome probes) was used on cultured and uncultured, male, peripheral blood leukocytes. Specific red or orange × (or Y) and green Y (or X) signals were examined under fluorescence microscope equipped with a triple band-pass filter with 10X, 20X, and 40× objective lenses. The purpose was, using the present invention, to develop FISH procedures in which fluorescence signals in interphase nuclei could be enumerated unequivocally under the 40X, non-oil objective lens. In some cases, enumeration of interphase nuclei was accomplished with a 20× objective lens.

1) Solutions F and G Were Prepared as Set Forth in Example 1.

2) Denaturation-hybridization Solutions:

Hybridization with labeled probes containing formamide alone, glycerol alone or dextran sulfate alone did not promote hybridization. When FISH was performed with the solution G (containing glycerol and dextran sulfate) or solution F (containing formamide and dextran sulfate), hybridization signals were noticeably enhanced. From studies with various combinations of conceivable mixtures of chemicals, it was found that the above solutions (solutions F and G) were the most effective denaturation-hybridization media for FISH.

The concentration of dextran sulfate, should be at least 10%, or between 8%–12%. The effectiveness of hybridization was considerably decreased with concentrations under 5%. Alternatively, as dextran sulfate concentration was increased above 15%, the viscosity of the denaturation-hybridization solution was increased, resulting in decreased effectiveness of hybridization between target nucleic acid and labeled DNA probes.

In solution F, formamide played a significant role in the effectiveness of the hybridization in the absence of salts. As formamide concentration was increased in the presence of 10% dextran sulfate, the increased viscosity of the solution possibly reduced effective hybridization. In addition, high formamide concentrations induced irreversible structural damage on nuclear or chromosomal DNA during the FISH process. The optimal formamide concentration was determined to be at 20%±5%. With the concentration of formamide below 10%, the slides had a tendency to dry around the edge of the coverslip during hybridization in the absence of sealing with rubber cement. These dried slides did not exhibit fluorescence signals. With the formamide concentration above 30%, the slides showed extensive destruction of cellular or nuclear morphology under the denaturation-hybridization conditions of the present invention. Since formamide denatures and inactivates enzymes, solution F normally cannot be used for probes labeled with proteins or enzymes (e.g., horseradish peroxidase, β-galactosidase, or alkaline phosphatase). However, it appears that formamide can be used at limited concentrations (i.e., 20±5%) for effective hybridization with DNA/RNA specific probes. Samples treated with solution F have a tendency to dry faster due to evaporation of formamide during hybridization in a dry oven (or dry incubator) for an extended period of time without sealing with rubber cement. On the other hand, when hybridization was performed in a humidified incubator for an extended period of time (without the rubber cement), the samples had a tendency to absorb excessive moisture. Therefore, sealing with rubber cement is necessary to keep the slide from drying or from absorbing moisture during long hybridization periods.

Solution G was a highly versatile denaturation-hybridization medium. Although the exact roles played by glycerol and dextran sulfate during fluorescence in situ hybridization have not yet been determined, it appears that glycerol concentration plays an important role in the effectiveness of hybridization in the presence of dextran sulfate. In addition, in general glycerol has a tendency to stabilize and protect enzymes and proteins. The optimal glycerol concentration for effective in situ hybridization was in the 20%–30% range. The fluorescence signal was diminished considerably as the glycerol concentration was increased above 35% or decreased under 10% concentration. However, by adjusting the glycerol concentration between 20% to 50% in conjunction with 10% dextran sulfate, hybridization temperature and hybridization time can be varied without losing the effectiveness of hybridization or the ability to detect signals. Glycerol concentrations of 20%–50% required a longer hybridization time to achieve hybridization signals. Sealing with rubber cement was not needed.

3) Temperature and Time for Denaturation of Probes and Nucleic Acids in Cells:

Studies of peripheral lymphocytes using denaturation temperatures ranging from 80° C. to 115° C., determined that simultaneous denaturation of target nucleic acid and labeled probes (without sealing the coverslips with rubber cement) gave the brightest fluorescence signals when the denaturation process was performed in either solution F or solution G. The fluorescence signals were considerably diminished by denaturation temperatures below 85° C. or above 110° C. Therefore, it appeared that denaturation of the target nucleic acid was most effective at 95° C.–105° C. (100° C.±5° C.) in the presence of solution F or G.

It was determined that the optimal denaturation time at 95° C.–105° C. was for 1.5±0.5 minutes. Denaturation for less than 1 minute and longer than 2 minutes at 100° C.±50° C. caused diminished hybridization signals. The intensity of hybridization signals was almost identical between solutions F and G under these conditions.

TABLE I

DENATURATION
Time and Temperature varied
Hybridization: constant at 5 minutes at 55° C.

|  | 90° C. | 100° C. | 105° C. | 110° C. |
| --- | --- | --- | --- | --- |
| 0.5 MIN | 0 | ± | 1+ | 1.5+ |
| 1.0 MIN | 1.5+* | 1.5+ | 3+ | 2+ |
| 1.5 MIN | 2+ | 4.5+ | 4.5+ | 3+ |
| 2.0 MIN | 2.5+ | 3+ | 3.5+ | 2.5+ |
| 2.5 MIN | 3+ | 2.5+ | 2.5+ | ± |
| 5.0 MIN | 3+ | 2+ | 1.5+ | 0 |

*Visualization with 20x dry objective lens: score: 1–5+ with 5+ brightest

4) Temperature and Time Hybridization

After the simultaneous denaturation of target nucleic acid and probes for 1.5±0.5 minutes at 100° C.±5° C., different hybridization temperatures were tested, from 38° C. to 90° C. for 5 minutes without sealing the coverslips with rubber cement. It was determined that 50° C.–60° C. (55° C.±5° C.) was the optimal condition for effective hybridization. As the hybridization temperature was lowered below 45° C. or raised above 60° C., the intensity of the fluorescence signals was markedly diminished. Therefore, it was determined that the optimal temperature for effective hybridization between target nucleic acids and labeled probes (in the presence of solution F or G) was 55° C.±5° C.

A 5-minute hybridization period was adequate under the above experimental conditions for enumeration of signals in interphase nuclei with a 40× dry objective lens, although incubation for a total of 20–30 minutes enhanced the hybridization signals, allowing enumeration of fluorescence signals with a 20× dry objective lens. Under 20X dry objective lens, the size of nuclei was too small to enumerate.

TABLE II

HYBRIDIZATION
Time & Temperature Varied
Denaturation Constant at 100° ± × 1.5 minute

|  | 38° C. | 45° C. | 55° C. | 65° C. | 75° C. |
| --- | --- | --- | --- | --- | --- |
| 2 MIN | 0 | 0 | 1+ | 2+ | 1+ |
| 5 MIN | 0 | 0 | 3+ | 3+ | 2+ |
| 10 MIN | 0 | 0 | 3+ | 3+ | 2+ |
| 15 MIN | 0 | 0 | 4+ | 4+ | 2+ |
| 30 MIN | ± | ± | 5+ | 3+ | 2+ |
| 60 MIN | 1+* | 2+ | 5+ | 2.5+ | 2+ |
| OVERNIGHT | 5+* | 5+ | 5+ | 3+ | 1+ |

*Visualization with 20x dry objective lens: score: 1–5+; 5+ brightest

Alternatively, sample slides were placed on an aluminum shelf for denaturation for 1.5±0.5 minutes at 100°±5° C. The slides and shelf were put into a drawer of a laboratory bench for 5 minutes, and were cooled spontaneously by ambient air temperature of the laboratory. This also resulted in effective hybridization. The fluorescence signals observed, under these conditions, were almost identical to those observed by hybridization at 55° C.±5° C. for 5 minutes as described above.

Since both the above hybridization procedures were very effective in the detection of fluorescence hybridization signals in 15 minutes, there was no need for overnight hybridization with this invention.

The following three procedures, however, were performed to determine the effectiveness of overnight hybridization.

(a) The denatured slides were incubated overnight in a dry incubator or oven at approximately 38° C. No sealing between coverslip and glass slide with rubber cement was done. The following morning, the slides were subjected directly to the post-hybridization washings (see below). Bright hybridization signals were obtained, which enabled performance of signal enumeration with a 40× dry lens.

(b) The denatured slides were put inside a drawer of a laboratory bench at ambient temperature overnight. No sealing between coverslip and glass slide with rubber cement was performed. The following morning, the slides were directly subjected to the post-hybridization washings (see below). Some of the slides were incubated at 55° C.±5° C. for 5 minutes before the post-hybridization washings. In either case, bright hybridization signals were visualized so that the analysis was able to be performed with a 40× dry objective lens. Therefore, there was no need to re-hybridize at 55° C.

(c) After denaturation at 95° C.–105° C. for 1.5 minutes, the hot aluminum shelf containing denatured slides was put inside a drawer of a laboratory bench overnight; the slides on the aluminum shelf cooled spontaneously and were left overnight. No sealing between coverslip and glass slide with rubber cement was performed. The following morning, the slides were subjected to the post-hybridization washings (see below). Bright hybridization signals were visualized with a 40× dry objective lens.

From these studies, it was determined that the present invention does not require another hybridization step after leaving the denatured slides (on or off the hot aluminum oven shelf) at room temperature overnight in the laboratory. It appears that standing overnight at ambient temperature, hybridization fully occurred spontaneously for solution G.

Since solution F dries faster, overnight hybridization at room temperature or in a dry incubator of 38° C., without sealing with rubber cement, was not attempted for solution F. However, strong hybridization signals were observed when the overnight hybridization was performed with rubber cement. On the other hand, as noted above, effective hybridization signals were obtained with overnight hybridization in solution G, without resorting to rubber cementing. The presence of glycerol in solution G kept the samples from drying.

5) Post-hybridization Washings and Visualization of Signals:

The hybridized slides (after removing coverslips) were soaked in 50% formamide/0.45% NaCl at 38° C. for 3 minutes to remove excessive probes or non-specifically bound probes, and subsequently placed in 0.9% NaCl for 5 minutes at 38° C. to remove formamide.

Alternatively, formamide-free washing was achieved by immersing the hybridized slides into 0.1%–0.2% NaCl for 5 minutes at 60° C., and repeated again for another 3 minutes in fresh 0.1%–0.2% NaCl at 60° C.

After air drying, the slides were counterstained with DAPI (for Rhodamine signals) or PI (for FITC signals) for microscopic visualization. Under the above conditions, both formamide-containing and formamide-free washing procedures were very effective in removing non-specifically bound labeled probes.

The present invention allows the elimination of formamide from the entire FISH procedure; therefore, the present invention is both economical, since formamide is expensive, and advantageous in terms of preventing hazards to health, since formamide is a toxic chemical.

EXAMPLE 3

FISH with solution F and G using digoxygenin-labeled × and biotin-labeled Y (or biotin-labeled × and dioxygenin-labeled Y). (Indirect FISH)

A mixed probe of digoxygenin-labeled × and biotin-labeled Y probes (or biotin-labeled × and digoxygenin-labeled Y probes) were obtained from commercial sources. The probes were diluted with denaturation-hybridization F or G solution.

The in situ hybridization process (e.g., denaturation and hybridization and post-hybridization washings) was performed as described under Example 1. After post-hybridization washings, the slides were air-dried. An appropriate amount of a mixture of rhodamine-conjugated anti-digoxygenin (available from various commercial sources) and FITC-conjugated-avidin (available from various commercial sources) was applied to the slides. Alternatively, a mixture of rhodamine-conjugated and FITC-conjugated-anti-digoxigenin can be applied to the slides. The slides were then incubated at 38° C. for 5 minutes in a humidified incubator. The slides were washed in PBS (phosphate-buffered saline) 2 minutes each for three times. The slides were then air-dried. A small amount of counterstain (DAPI or PI) was spotted on the slides to counterstain before visualization under a microscope, as described under Example 1. Under these experimental conditions, no oil immersion lens was necessary for analysis. Interphase nuclei signal enumeration by fluorescence was adequately performed with a 40× or 60× dry objective lens.

With this indirect FISH, the whole process took an additional 11 minutes due to an additional antibody reaction and subsequent washings. The entire indirect FISH protocol can be accomplished in about 30 minutes to 60 minutes.

EXAMPLE 4 mRNA FISH in fixed paraffin-embedded tissue sections using direct-labeled fluorescent and indirect-labeled RNA probes.

In this example paraffin-embedded placental tissue was deparaffinized, hydrated, and prehybridized and hybridized in a mixture of solution F and 0.1% Diethylpyrocarbonate (DEPC) using labeled RNA probes to detect mRNA in the nuclei or cytoplasm of placental tissue sections. The purpose was to determine if using the present invention facilitated mRNA FISH and produced clear signals. The present invention under conditions as described below allowed the mRNA FISH procedure to be completed in 24 hours or less. Prior art using radioisotope detection requires up to 15 days.

The tissue sample was cut to an appropriate size, fixed in 4% paraformaldehyde (overnight minimum) at 5° C.; then placed in 5% sucrose (overnight minimum) until processed, embedded in paraffin, and cut into tissue sections (TS). The TS were deparaffinized in xylene and hydrated through graded EtOH as defined in prior art.

The TS were placed in Proteinase K, 2.5 ug/ml to 10 ug/ml, digested for 30 minutes to 1½ hours at 37° C. and washed 3 times in phosphate-buffered saline (PBS). The TS then were prehybridized in a mixture of solution F and DEPC (without probe) for 1 hour at 37° C., washed 3 times with PBS; excess PBS was removed by shaking.

The probe was diluted in solution F-DEPC at 20 ng/ml to 200 ng/ml and was added to the sample (approximately 12.5 ul/sample or enough to cover the sample), and a cover glass was placed over the sample. The cover glass was sealed with rubber cement for overnight hybridization; rubber cement was not necessary for hybridization of 5 hours or less.

The TS were placed in an oven at a temperature of 55° C. to 90° C. for 3 hours to 24 hours dependent upon the probe concentration. The cover glasses were removed, and the samples were washed for 7 minutes in 0.15% NaCl at 60° C. 15 ul of antifade (Vector Laboratories) were placed on each sample and cover glassed. The slide was viewed with a Texas red triple bandpass filter on a fluorescence microscope using a 60× dry objective lens. Signal was seen in the cytoplasm.

EXAMPLE 5

DNA FISH in fixed paraffin-embedded tissue sections using direct-labeled fluorescent and indirect-labeled DNA probes.

In this example paraffin-embedded tissue sections were deparaffinized, rehydrated, denatured and hybridized in solutions F and G. The purpose was to determine the effectiveness of the present invention for DNA FISH in fixed paraffin-embedded tissue.

The tissue and tissue sections (TS) were prepared as set forth in Example 4. The probe (Imagenetics/Vyses, Inc., Oncor Inc., BDS, Inc.) was diluted to 1 ul to 99 ul, approximately 12.5 ul/sample or enough to cover the sample was added and a cover glass was placed over the sample. The cover glass was sealed with rubber cement denatured at 100° C. to 110° C. for 1.5 minutes, then subjected to overnight hybridization; rubber cement was not used for hybridization times of 5 hours or less. The TS were placed in a hybridization oven at a temperature of 55° C. to 90° C. for 3 hours to 24 hours. The cover glasses were removed and the samples were washed for 7 minutes in 0.15% NaCl at 60° C. 15 ul of a mixture of antifade (Vector Laboratories) and counterstain (DAPI or PI) were placed on each sample and cover glassed. The slide was viewed with a Texas red triple bandpass filter on an epifluorescence microscope; signals were visualized with a 40× dry objective lens in the interphase nuclei.

EXAMPLE 6

DNA FISH in Peripheral blood mononuclear cells (PBMC) and polymorphonuclear cells (PMN) using different fixatives and direct-labeled fluorescent and indirect-labeled DNA probes.

In this example, different fixatives were used with the direct-labeled fluorescent and indirect-labeled DNA probes. The purpose was to demonstrate the versatility of the present invention with various fixatives. Peripheral blood was collected in an anticoagulant tube, and the PBMN and PNM were separated as described in prior art and fixed in several fixatives: 1) 3:1 Methanol:Glacial acidic acid (MeOH:Hac) fixative for a minimum of 30 minutes at −20° C., 2) 4% paraformaldehyde for 30 minutes to 3 hours and then applied to slides for and air dried for processing, 3) Methanol for 30 minutes minimum at −20° C.

Fixatives (1) The 3:1 MeOH:Hac fixation method has been previously described in Example 1.

(2) The paraformaldehyde fixed cells on air dried slides were treated with proteinase K at 2.5 ug/ml to 10 ug/ml and digested for 30 minutes to 1½ hours at 37° C. and washed 3 times in PBS.

(3) The cells were vortexed on high speed, and −20° C. methanol added a few drops at a time to a total of 8 ml. The cells were then placed in a −20° C. freezer for a minimum of 30 minutes. Following each fixative method described above, the samples were processed by the previously described optimal methods in this patent (Example 1). The slides were viewed with a Texas red triple bandpass filter on a fluorescent microscope; signals were observed with a 40× dry objective in the interphase nuclei.

EXAMPLE 7

FISH in Fetal cells from the maternal peripheral blood circulation fixed in 3:1 MeOH/Hac using direct-labeled fluorescent and indirect-labeled DNA probes.

Maternal peripheral blood was collected in an anticoagulant tube, and the fetal cells were separated as described in prior art and fixed in 3:1 MeOH:Hac fixative for a minimum of 30 minutes at −20° C. The samples were centrifuged at 1000 g's for 10 minutes, and 10 ul of sample were applied to each slide (12 mm fluorescent antibody circle) until a density of cells was reached sufficient for analysis.

7 ul of the diluted probe were then added to sample, and a cover glass was placed over the sample. The samples were processed by previously described optimal methods in this patent (Example 1). The slide was viewed with a Texas red triple bandpass filter on an epifluorescent microscope.

EXAMPLE 8

FISH in Sperm and noncultured Amniocytes fixed in 3:1 MeOH/Hac using direct-labeled fluorescent and indirect-labeled DNA probes.

The preparation of sperm and noncultured amniocytes for FISH was identical.

Aliquots of sperm or amniocytes were placed into 15 ml centrifuge tubes. PBS-containing 2 mM Dithiothreitol (DTT) was added to sperm or amniocytes at a concentration of 10 to $20 \times 10^6$ per ml for 45 minutes at room temperature to decondense the chromatin; the tubes were then centrifuged at 160 gs for 5 minutes. Supernatant was discarded, 8 ml −20° C. 3:1 MeOH/Hac were added and the sample was vortexed. The samples were fixed at −20° C. 3:1 MeOH:Hac for a minimum of 30 minutes. Preferable fixation time is overnight at −20° C. The sperm or amniocyte samples were centrifuged at 1000 g for 10 minutes. The supernatant was removed, and samples were resuspended in an appropriate volume of 3:1 MeOH:Hac. 10 ul of samples suspended in fixatives were placed on the slide (12 mm circle) assuring an even distribution. The slides were air dried for a minimum of 5 minutes. 7 ul of DNA probe (Imagenetics/Vysis, Inc.; Oncor, Inc.; BDS, Inc.) diluted (1 ul to 99 ul) in Solution F or G were added to each 12 mm circle and covered with a 12 mm round cover glass. The samples were processed by previously described optimal methods in this patent (Example 1). The samples were viewed and counted using a fluorscence microscope with a Texas red triple band pass filter with a 60× dry objective lens.

The preceding examples can be repeated with similar success by substituting the generically or specifically described reactants and/or operating conditions of this invention for those used in the preceding examples. Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference.

What is claimed is:

1. A hybridization solution for performing an in situ hybridization procedure, said solution consisting essentially of:

between about 8 and 12 percent by weight dextran sulfate;

between about 10 and 30 percent by volume formamide; and a salt.

2. The solution of claim 1 wherein said salt is selected from the group consisting of NaCl, KCl and saline sodium citrate.

3. A hybridization solution for performing an in situ hybridization procedure, said solution consisting essentially of:

between about 8 and 12 percent by weight dextran sulfate;

between about 10 and 30 percent by volume formamide;

a salt; and diethylpyrocarbonate.

4. A hybridization solution for performing an in situ hybridization procedure, said solution consisting essentially of:

between about 15 and 25 percent by weight glycerol;

between about 8 and 12 percent by weight dextran sulfate; and a salt.

5. The solution of claim 4 wherein said salt is selected from the group consisting of NaCl, KCl and saline sodium citrate.

6. The solution of claim 4 wherein said salt is about 0.9% by weight of said solution.

7. A hybridization solution for performing an in situ hybridization procedure, said solution consisting essentially of:

between about 15 and 25 percent by weight glycerol;

between about 8 and 12 percent by weight dextran sulfate;

a salt; and diethylpyrocarbonate.

8. A process for fluorescence in situ hybridization (FISH) comprising the steps of:

denaturation;

hybridization in 5 minutes or less; and post-hybridization;

wherein the steps of denaturation and hybridization occur in the absence of a fixer for a sample on a substrate.

9. The process of claim 8 wherein the step of denaturation is conducted for 1 to 2 minutes.

10. The process of claim 9 wherein the step of denaturation occurs at about 95° C. to 105° C.

11. The process of claim 8 wherein the step of post-hybridization is conducted for 5 to 10 minutes.

12. The process of claim 9 wherein the step of post-hybridization occurs at about 55° C. to 65° C.

13. The process of claim 8 wherein the step of hybridization occurs in a solution, the solution comprising:

between about 8 and 12 percent by weight dextran sulfate;

between about 10 and 30 percent by volume formamide; and a salt.

14. The process of claim 13 wherein the solution further comprises diethylpyrocarbonate.

15. The process of claim 8 wherein the step of hybridization occurs in a solution comprising dextran sulfate and glycerol.

16. The process of claim 15 wherein the solution further comprises diethylpyrocarbonate.

17. The process of claim 15 wherein the solution further comprises a salt.

18. The process of claim 8 wherein the steps of denaturation and hybridization occur in the absence of formamide.

19. The process of claim 8 wherein the step of post-hybridization comprises washing in the absence of formamide.

20. The process of claim 8 wherein the sample is selected from the group consisting of fixed paraffin-embedded tissue, frozen tissue sections, cultured cells, and uncultured cells; and wherein the sample is prepared on a medium selected from the group consisting of nitrocellulose paper, nylon paper and media used in blotting techniques.

21. The process of claim 8 wherein the step of hybridization occurs at about 45° C. to 60° C.

22. The solution of claim 1 wherein said salt is approximately 0.9% by weight of said solution.

23. The process of claim 8 wherein the step of denaturation is conducted in 5 minutes or less.

* * * * *